United States Patent [19]

Smith et al.

[11] Patent Number: 4,827,013
[45] Date of Patent: May 2, 1989

[54] (S) α-(CYANO-3-PHENOXY-BENZYL ACETATE

[75] Inventors: Frank J. Smith; Jerry M. Roper, both of Baton Rouge, La.

[73] Assignee: Ethyl Corporation, Richmond, Va.

[21] Appl. No.: 815,207

[22] Filed: Dec. 31, 1985

[51] Int. Cl.$^4$ ............................................ C07C 121/66
[52] U.S. Cl. ..................................................... 558/406
[58] Field of Search ................. 558/406, 410; 514/521

[56] References Cited

U.S. PATENT DOCUMENTS

| 4,091,010 | 5/1978 | Norton | 558/351 |
| 4,113,763 | 9/1978 | Norton | 558/345 |
| 4,234,505 | 11/1980 | Photis | 558/406 |
| 4,273,727 | 6/1981 | Martel et al. | 558/410 |
| 4,582,646 | 4/1986 | Stoutamire et al. | 558/406 |
| 4,594,196 | 6/1986 | Stoutamire et al. | 558/410 |

OTHER PUBLICATIONS

C.A. 100:4816b (1984), Mitsuda et al.
C.A. 102:184844g (1985), Sumitomo Chem. Co. Ltd.

Primary Examiner—Joseph Paul Brust
Attorney, Agent, or Firm—W. G. Montgomery

[57] ABSTRACT (S) α-cyano-3-phenoxy-benzyl acetate having the formula:

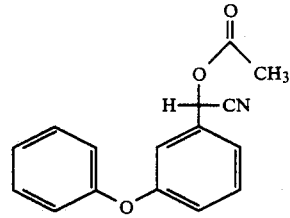

and a novel process for its preparation.

2 Claims, No Drawings

(S) α-(CYANO-3-PHENOXY-BENZYL ACETATE)

FIELD OF THE INVENTION

This invention relates to optically active (S) α-cyano-3-phenoxy-benzyl acetate and to a method for biologically preparing the same. More particularly, it relates to (S) α-cyano-3-phenoxy-benzyl acetate and to a method for preparing the same characterized by allowing a racemic mixture of (R,S) α-cyano-3-phenoxy-benzyl acetate to react with a lipase originated from a microorganism which is capable of asymmetrically hydrolyzing the ester of the (R) alcohol in the racemic mixture to give (R) α-cyano-3-phenoxy-benzyl alcohol and (S) α-cyano-3-phenoxy-benzyl acetate.

BACKGROUND OF THE INVENTION (R,S) α-cyano-3-phenoxy-benzyl acetate, which is a racemic mixture, is known.

European Patent Application No. 84300024.1 discloses a method for biologically preparing optically active (S) α-cyano-3- phenoxy-benzyl alcohol, which is the alcohol moiety of certain pyrethroids, by reacting an ester of racemic (R,S) α-cyano-3-phenoxy-benzyl alcohol with an esterase wherein the ester of (S) α-cyano-3-phenoxy-benzyl alcohol is predominantly hydrolyzed thereby permitting optical resolution of the (S)-isomer alcohol from the ester of its antipode. Thus, there is provided in the art a biological method capable of producing (R) α-cyano-3-phenoxy-benzyl acetate. Until Applicants' invention, however, there has existed no known method for producing the (S)-isomer of α-cyano-3-phenoxy-benzyl acetate insofar as Applicants are aware.

SUMMARY OF THE INVENTION

Thus, there is provided for the first time (S)α-cyano-3-phenoxy-benzyl acetate free of its (R) form. There is also provided a novel process for the preparation of (S)α-cyano-3-phenoxy-benzyl acetate.

THE INVENTION

The novel product of the invention is (S)α-cyano-3-phenoxy-benzyl acetate of the formula:

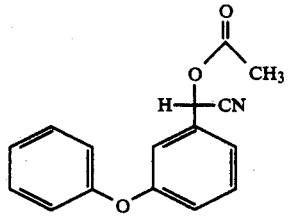

which has a positive specific rotation which is a value of about $[\alpha]_D 20 = +17.1°$ when measured at a concentration of 10% in benzene. The process of the invention for the preparation of (S) α-cyano-3-phenoxy-benzyl acetate comprises reacting (R,S) α-cyano-3-phenoxy-benzyl acetate with a lipase originating from a microorganism and capable of asymmetrically hydrolyzing the (R)α-cyano-3-phenoxy-benzyl acetate ester to give optically active (R) α-cyano-3-phenoxy-benzyl alcohol and (S) α-cyano-3-phenoxybenzyl acetate. The ester of the (S) alcohol and the (R) alcohol are then separated from the reaction mixture and thereafter the ester of the (S) alcohol is separated and recovered from the (R) alcohol.

The lipases employable in the present invention are those capable of asymmetrically hydrolyzing the ester of (R) α-cyano-3-phenoxy-benzyl alcohol and they are originated from microorganisms. One example of an employable lipase is a carboxylic acid hydrolase originated from the genus *Candida*, and particularly, the strain *Candida cylindricae*, also known as *Candida rugosa*. The enzyme is commercially available from the Sigma Chemical Company, Post Office Box 14508, St. Louis, Mo. 63178.

In practicing the process of the present invention, the asymmetric hydrolysis of the (R) ester is carried out by stirring or shaking a racemic mixture of (B,S) α-cyano-3-phenoxy-benzyl acetate and a lipase-containing liquor, such as a cultured liquor of such microorganism, its filtrate, lipase extracted liquor and its concentrate, a suspension of microorganism cells or aqueous solution containing crude or purified lipase preparation.

The process can be carried out at ambient conditions although it is preferred to carry out the reaction at elevated temperatures varying from about 40° C. to 50° C. since at elevated temperatures the reaction rates are much faster. The period of time for the reaction is typically from about 10 to 40 hours. However, the reaction time can be shortened by increasing the reaction temperature or by increasing the concentration of enzyme.

It is essential to control the pH of the reaction medium during the asymmetric hydrolysis reaction because α-cyano-3-phenoxy-benzyl alcohol tends to decompose when exposed to a basic substance. That is, exposure to a basic medium results in the decomposition of the alcohol although the hydrolysis reaction proceeds. Accordingly, the hydrolysis reaction should be conducted at a pH no higher than pH 8. Furthermore, a pH which is too low will cause deactivation of the enzyme. Thus, the reaction is preferably conducted in the range of pH 4 to pH 8, most preferably pH 5 to pH 6. A buffer solution may be used to prevent the lowering of the pH value due to the formation of organic acid during the course of hydrolysis. Either an inorganic or organic salt buffer can be used as the buffer solution.

After the asymmetric hydrolysis reaction, the (S) α-cyano-3-phenoxy-benzyl acetate ester and the (R) alcohol are separated from the reaction mixture by solvent extraction, liquid phase separation by standing, column chromatography or other conventional separation techniques. The ester is then separated from the alcohol by chromatography, preferably chromatography over silica gel.

Methods for producing the racemic mixture of (R,S) α-cyano-3-phenoxy-benzyl acetate from which the (S) α-cyano-3-phenoxy-benzyl acetate is obtained by the method of the present invention are known in the art. For example, an alkali metal cyanide, such as sodium cyanide, can be reacted with 3-phenoxybenzyldehyde and acetyl chloride in methylene chloride containing tetrabutylammonium bromide (Chem. Abstracts, 96(25):217504j) to produce the racemic mixture.

(S) α-cyano-3-phenoxy-benzyl acetate is useful as an intermediate for the production of synthetic pyrethroids such as fenvalerate, cypermethryn, and decamethrin and is deemed to possess insecticidal, herbicidal and bactericidal activities of its own.

The present invention is further described by means of the following examples. However, it is to be understood that the invention is not intended to be limited by these examples.

EXAMPLE 1

To 123 milliliters of 0.2 M concentration of a sodium acetate buffer solution (pH 5.0) were added 30 grams of (R,S)α-cyano3-phenoxy-benzyl acetate and 2.25 grams of *Candida cylindricae* lipase. The mixture was incubated with stirring at 50° C. for 23 hours. Samples were removed periodically and analyzed by gas chromatography. At the end of the 23-hour reaction period, it was determined that the mixture contained 53% α-cyano-3-phenoxy-benzyl alcohol and 47% α-cyano-3-phenoxy-benzyl acetate.

The reaction mixture was then extracted with toluene. The toluene extract was concentrated by vacuum distillation to yield a yellow oil. The yellow oil was mixed with 123 milliliters of 0.2 M concentration of a sodium acetate buffer solution (pH 5.0) and 2.25 grams of *Candida cylindricae* lipase. The mixture was incubated with stirring at 25° C. for 18 hours and extracted with toluene as described above to yield a yellow oil containing 37% α-cyano-3-phenoxy-benzyl acetate, 45% α-cyano-3-phenoxy-benzyl alcohol and 15% m-phenoxybenzaldehyde as determined by gas chromatography.

The oil was then extracted with 15 equal volumes petroleum: ether (boiling point 35°–60° C.). These fractions were combined and concentrated by vacuum distillation to yield a yellow oil containing 67% α-cyano-3-phenoxy-benzyl acetate, 15% α-cyano3-phenoxy-benzyl alcohol and 17% m-phenoxybenzaldehyde. This oil was analyzed on NMR using a chiral shift reagent [Eu(C$_{12}$H$_{14}$Fe$_3$O$_2$)]. The analysis showed that the α-cyano3-phenoxy-benzyl acetate consisted only of (S)α-cyano-3-phenoxybenzyl acetate.

The (S)α-cyano-3-phenoxy-benzyl acetate was purified by column chromatography. The oil was placed on a column containing Kieselgel 40 (60–230 mesh) and eluted with a mixture of heptane and ethyl acetate in a ratio of 85 parts heptane to 15 parts ethyl acetate. The fractions containing only (S)α-cyano-3-phenoxybenzyl acetate were combined and concentrated by vacuum distillation to yield a yellow oil. The oil (116 milligrams) was combined with enough benzene to bring the total volume to 1.16 milliliters. The benzene solution was analyzed on a Perkin-Elmer Model 241 Polarimeter and yielded a positive rotation of +17.1° at 20° C.

EXAMPLE 2

To 886 milliliters of 0.2 M concentration of a sodium acetate buffer solution (pH 5.0) were added 100 grams of (R,S)α-cyano-3-phenoxy-benzyl acetate and 6.0 grams of *Candida cylindricae* lipase. The mixture was incubated with rapid stirring at room temperature for 18 hours. With the cessation of stirring, the mixture separated into two phases. The lower, oily phase was collected and centrifuged to remove the enzyme. The protein was washed with toluene and the toluene fraction was added to the supernatant oil. The combined fractions were washed with NaCl saturated water and then dried over anhydrous magnesium sulfate. The toluene was removed by vacuum distillation to yield 68.9 grams of yellow oil.

The yellow oil was placed on a column containing Kieselgel 40 (60–230 mesh) and eluted with heptane:ethyl acetate (65:35). Fractions were collected and concentrated by vacuum distillation. Three fractions were obtained. These contained, respectively, 23.2 grams of α-cyano-3-phenoxy-benzyl acetate, 4.5 grams of α-cyano-3-phenoxy-benzyl alcohol, and a mixture of α-cyano-3-phenoxy-benzyl acetate and α-cyano-3-phenoxy-benzyl alcohol.

The α-cyano-3-phenoxy-benzyl acetate fraction was analyzed on NMR using a chiral shift reagent [Eu(C$_{12}$H$_{14}$F$_3$O$_2$)$_3$]. Analysis showed that the α-cyano-3-phenoxy-benzyl acetate consisted of a mixture containing 75–85% (S)α-cyano-3-phenoxy-benzyl acetate and 15–25% (R)α-cyano-3-phenoxy-benzyl acetate.

The α-cyano-3-phenoxy-benzyl alcohol fraction was analyzed by high performance liquid chromatography as described in Example 1. The α-cyano-3-phenoxy-benzyl alcohol fraction consisted exclusively of (R)α-cyano-3-phenoxy-benzyl alcohol.

We claim:

1. (S) α-cyano-3- phenoxy-benzyl acetate of the formula:

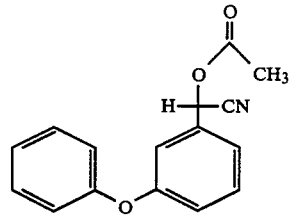

free of its (R) form said acetate being of the specific rotation of about [α]$_D$20= +17.1° when measured at a concentration of 10% in benzene.

2. The acetate of claim 1 with a specific rotation of [α]$_D$20= +17.1° measured at a concentration of 10% in benzene.

* * * * *